United States Patent [19]

Beranek

[11] Patent Number: 4,592,372

[45] Date of Patent: Jun. 3, 1986

[54] PACING/SENSING ELECTRODE SLEEVE AND METHOD OF FORMING SAME

[75] Inventor: William J. Beranek, Cooper City, Fla.

[73] Assignee: Cordis Corporation, Miami, Fla.

[21] Appl. No.: 612,855

[22] Filed: May 22, 1984

[51] Int. Cl.$^4$ ............................................. A61N 1/04
[52] U.S. Cl. ................................. 128/786; 128/419 P
[58] Field of Search ................... 128/419 P, 783, 784, 128/786, 639, 642

[56] References Cited

U.S. PATENT DOCUMENTS

| | | | |
|---|---|---|---|
| 3,568,660 | 3/1971 | Crites | 128/2 |
| 3,664,347 | 5/1972 | Harmjanz | 128/404 |
| 3,769,984 | 11/1973 | Muench | 128/404 |
| 3,825,015 | 7/1974 | Berkovits | 128/404 |
| 3,942,536 | 3/1976 | Mirowski et al. | 128/419 D |
| 3,995,623 | 12/1976 | Blake et al. | 128/2.06 E |
| 4,280,511 | 7/1981 | O'Neill | 128/784 |
| 4,412,531 | 11/1983 | Magovern et al. | 128/419 P |
| 4,437,474 | 3/1984 | Peers-Trevarton | 128/419 P |
| 4,458,695 | 7/1984 | Peers-Trevarton | 128/419 P |

OTHER PUBLICATIONS

Mercer, "Design, Fabrication, and Testing of Silicon, Molybdenum, and Tungsten Microelectrode Arrays for Biostimulation", Stanford Electronics Laboratories Technical Report 5306-2, May 1976, pp. 45-75.

Primary Examiner—William E. Kamm
Assistant Examiner—Mitchell J. Shein
Attorney, Agent, or Firm—Henry W. Collins; Thomas R. Vigil

[57] ABSTRACT

The pacing lead comprises a catheter and first and second conductors in the catheter. A tip electrode is fixed to the distal end of the catheter and in electrical contact with a distal end of the first conductor within the catheter. The catheter has an opening in the wall thereof with a bared end portion of the second conductor extending through the opening, out of the catheter and around the catheter. A thin walled electrode sleeve made of a rhenium/tungsten alloy is positioned about and in direct electrical contact with the bared end portion of the second conductor and is compressed about the conductor end portion and the catheter to an extent where the outer diameter of the sleeve is substantially the same as the outer diameter of the catheter.

The method for making a pacing lead comprises the steps of: fixing a tip electrode onto the distal end of a flexible catheter; connecting a distal end of a first wire conductor fed through the flexible catheter to the tip electrode; feeding a second wire conductor part way into the flexible catheter and through an opening in the wall of the catheter; baring the distal end portion of the second wire conductor; coiling the bared end of the second wire conductor about the catheter; positioning an electrode sleeve made of a rhenium/tungsten alloy over the coiled bared conductor end portion and catheter; and compressing the sleeve over the coiled bare wire conductor end portion such that the outer diameter of the sleeve is substantially the same as the outer diameter of the catheter.

13 Claims, 4 Drawing Figures

U.S. Patent  Jun. 3, 1986  4,592,372
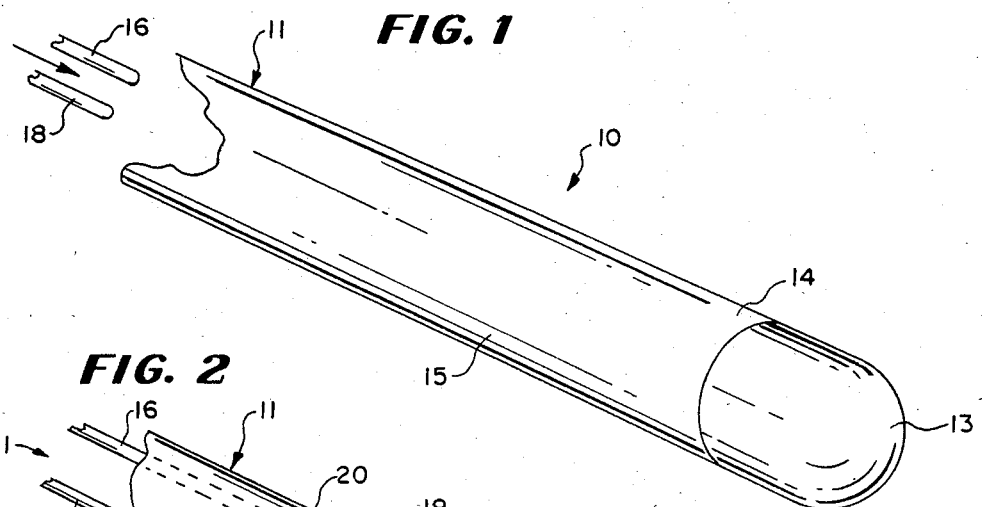
FIG. 1
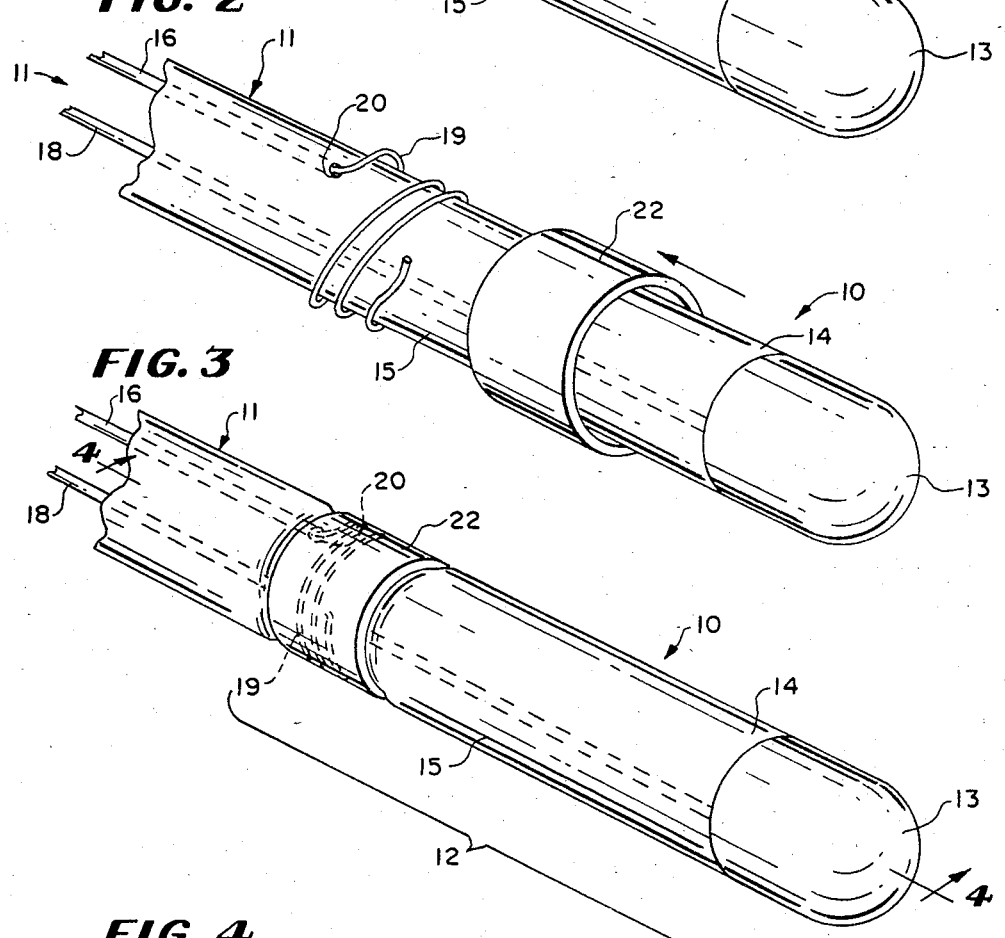
FIG. 2
FIG. 3
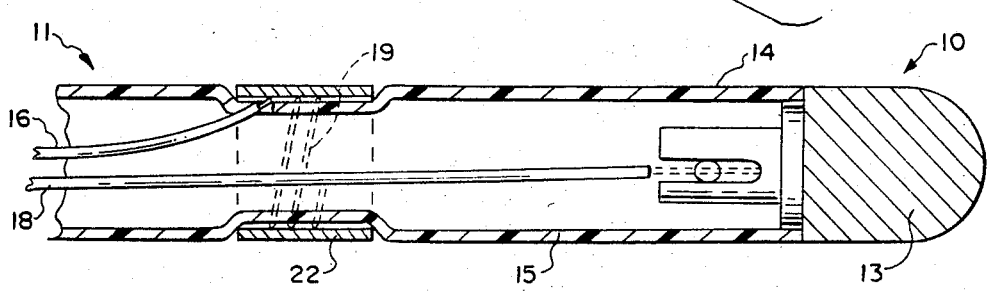
FIG. 4

PACING/SENSING ELECTRODE SLEEVE AND METHOD OF FORMING SAME

BACKGROUND OF THE INVENTION

1. Field of the Invention

The present invention relates to multi-electrode pacing/sensing leads. More specifically, the invention relates to a new material utilized in electrode sleeves in an isodiametric multi-electrode pacing/sensing lead.

2. Description of the Prior Art

Heretofore, various materials have been proposed for use in the formation of electrode sleeves. Such materials have included stainless steel, elgiloy, platinum/irridium, tantalum or MP35N. All of these materials have exhibited properties required of such electrode sleeve material, such properties being ductility, radio-opacity and a desired degree of impedance to signal transmission to and from organic tissue.

Various methods of forming ring or sleeve electrodes have been proposed. Several examples of methods for forming and the sleeve electrodes formed thereby are disclosed in the following U.S. Patents:

| U.S. Pat. No. | PATENTEE |
|---|---|
| 3,942,536 | Mirowski et al |
| 3,664,347 | Harmjanz |
| 3,568,660 | Crites |
| 3,995,623 | Blake et al |
| 3,769,984 | Muench |
| 3,825,015 | Berkovits |
| 4,280,511 | O'Neill |

The Mirowski et al U.S. Pat. No. 3,942,536 discloses a cardioverting device having a single intravascular catheter wherein proximal and distal electrode assemblies on a catheter each comprise a plurality of spaced apart conductive metal rings. The rings are made of solid platinum irridium and are fitted snugly about a molded silicone rubber casing, with a spacing between the rings being provided to allow for flexibility of the electrode.

The Harmjanz U.S. Pat. No. 3,664,347 discloses an electric heart stimulation device wherein a filament or tubing of polyurethane is received over a plastic core. Between the filament and the core are two flexible wire conductors with portions of the filament cut away to expose the conductors at the desired locations. Sleeve electrodes can be slid over the tubing to contact the exposed conductors.

The Crites U.S. Pat. No. 3,568,660 discloses a pacemaker catheter which comprises a thin first layer of rubber over the exterior surface of a length of flexible tubing, and at least two electrical conductors helically wound over the surface of the tubing and embedded within the layer of rubber. An end portion of each conductor is then extracted from the rubber and wound around the tubing. Metal contact sleeves are then placed over the wound end portions to form spaced electrodes.

The Blake et al U.S. Pat. No. 3,995,623 discloses a catheter which is flow directed through the heart by a balloon on its distal end. The catheter preferably comprises two distal and three proximal electrodes, all of which are identical. Each electrode comprises a split collar of spring metal with the ends slidably overlapping. Each collar has an inner diameter slightly smaller than the outer diameter of the catheter over which they are positioned. Once the collars are relaxed, they grip the surface of the tube. The tube is softened by heating, allowing each collar to further contract into the body of the catheter to lock each electrode in a fixed position on the catheter. Each electrode is further sealed to the tube by annular deposits of adhesive.

The Muench U.S. Pat. No. 3,769,984 discloses a bipolar transverse pacing catheter with conductors therein formed of stranded tantalum which conductors are connected to respective electrodes by means of crimp rings. The crimp rings are also preferably formed of tantalum.

The Berkovits U.S. Pat. No. 3,825,015 discloses a single catheter that provides for separate electrical stimulation to the atrium or ventricle of a heart on mutually related conductors. The conductors within the catheter are welded to respective conductive rings, the rings being made from a platinum compound. The conductors themselves may be ordinary conductive copper wire or coiled wire. Means are provided for preventing electromagnetic interference between the atrial and ventricular stimulating conductors.

The O'Neill U.S. Pat. No. 4,280,511 discloses a multi-electrode lead assembly wherein an isodiametric multi-electrode assembly is formed by provision of a ring electrode of undisclosed material swaged into the lead insulation and wherein a soft metal such as silver is utilized between the ring electrode and a coiled wire core to provide electrical contact therebetween. A hole for the silver slug or ball is provided in a catheter wall.

Also, an isodiametric continuous non-split sleeve electrode received about and over a bared end of a wire conductor which is looped and knotted about a tubing in a pacing lead electrode assembly is disclosed in copending application Ser. No. 377,461 for: CARDIAC LEAD HAVING MULTIPLE RING ELECTRODES.

As will be described in greater detail hereinafter, the electrode sleeve of the present invention is fabricated from a rhenium/tungsten alloy and is crimped or swaged around a catheter in the area of the catheter where a conductor is brought from within the catheter through the catheter wall and wrapped in a coil around the exterior of the catheter. The electrode sleeve is swaged or crimped to compress the sleeve against the catheter wall thereby providing a uniform external diameter to the lead assembly then formed.

The rhenium/tungsten alloy material provides high ductility, radio-opacity and low impedance in signal transmission through living tissue.

Although the use of a rhenium/tungsten alloy per se as an electrodematerial has been proposed, the use of a rhenium/tungsten material in a medical implant has not heretofore been proposed.

Examples of rhenium/tungsten alloy electrodes used in other environments are disclosed in the following U.S. patents:

| U.S. Pat. No. | PATENTEE |
|---|---|
| 1,877,261 | Weiger |
| 2,391,458 | Hensel |
| 3,307,198 | Morgan |
| 3,359,082 | Dickinson et al |
| 3,508,975 | Osovitz et al |
| 3,573,903 | Delgrosso |

The Weiger U.S. Pat. No. 1,877,261 discloses electrical make-and-break contacts for closing and opening electrical circuits with the contacts being formed from rhenium or an alloy containing rhenium, such as an alloy of rhenium and tungsten.

The Hensel U.S. Pat. No. 2,391,458 discloses metallic electrodes suitable for use in spark plugs, ignition systems, high frequency generators, high frequency induction furnaces, etc. The electrodes may be formed of various compositions, one of which is a rhenium plated rod having a core of tungsten, molybdenum or an alloy of tungsten and copper, or tungsten and silver.

The Morgan U.S. Pat. No. 3,307,198 discloses an electrode material for use in electrostatic recording heads comprising an alloy of tungsten and rhenium.

The Dickinson U.S. Pat. No. 3,359,082 and the Delgrosso U.S. Pat. No. 3,573,903 discloses various rhenium/tungsten alloys and methods for forming same.

The Osovitz et al U.S. Pat. No. 3,508,975 discloses a rhenium/tungsten alloy thermocouple with compensating lead wires.

As will be described in greater detail hereinafter the present invention differs from the various electrodes disclosed in the prior art patents listed above by providing a rhenium/tungsten electrode sleeve in an electrode assembly at the end of a pacing lead. Such an electrode sleeve has superior properties to ring electrodes presently in use in pacing lead electrode assemblies.

SUMMARY OF THE INVENTION

According to the invention, there is provided a pacing/sensing lead comprising a catheter; first and second conductors in said catheter; a tip electrode fixed to the distal end of said catheter and in electrical contact with a distal end of said first conductor within said catheter; said catheter having an opening in the wall thereof; a bared end portion of said second conductor extending through said opening, out of said catheter, and around said catheter; a thin walled electrode sleeve made of a rhenium/tungsten alloy positioned about and in direct electrical contact with said bared end portion of said second conductor and compressed about said conductor end portion and said catheter to an extent where the outer diameter of said sleeve is substantially the same as the outer diameter of said catheter said alloy having as its major component at least 80% rhenium by weight.

Further, according to the invention there is provided a method for making a pacing/sensing lead comprising the steps of: fixing a tip electride onto the distal end of a flexible catheter; connecting a distal end of a first wire conductor fed through the flexible catheter to said tip electrode; feeding a second wire conductor part way into the flexible catheter and through an opening in the wall of said catheter; baring the distal end portion of said second wire conductor; coiling the bared end of said second wire conductor about the catheter; positioning an electrode sleeve made of a rhenium/tungsten alloy over the coiled bared conductor end portion and catheter; and compressing said sleeve over the coiled bare wire conductor end portion such that the outer diameter of said sleeve is substantially the same as the outer diameter of said catheter, said alloy having as its major component at least 80% rhenium by weight.

BRIEF DESCRIPTION OF THE DRAWINGS

FIG. 1 is a perspective view of a distal end of a pacing lead utilized in the formation of a multi-electrode lead assembly constructed according to the teachings of the present invention.

FIG. 2 is a perspective view of the distal end shown in FIG. 1 and shows an electrical wire conductor being brought through an opening in a catheter wall and wound therearound and a sleeve being placed over the distal end.

FIG. 3 is a perspective view of the distal end shown in FIG. 2 and shows the sleeve now crimped or swaged over the wound coiled wire conductor to form an electrode sleeve of the multi-electrode lead assembly of the present invention.

FIG. 4 is a sectional view taken along line 4—4 of FIG. 3.

DESCRIPTION OF THE PREFERRED EMBODIMENTS

Referring now to FIG. 1 in greater detail, there is illustrated therein a distal end 10 of a pacing lead 11. An electrode assembly 12 (FIG. 3) is formed at the distal end 10. The electrode assembly 12 includes a tip electrode 13 extending from and fixed to the distal end 14 of a flexible catheter 15 of the lead 11.

First and second wire conductors 16 and 18 are inserted, as shown, into the catheter 15 or the lead 11.

Referring now to FIG. 2, the wire conductors 16 and 18 are fed into the catheter 15 with the conductor 18 being fed to the tip electrode 13. Meanwhile a bared end portion 19 of the conductor 16 is brought out of the catheter 15 through an opening 20 in the wall of the catheter 15. The bared end portion 19 of the conductor 16 is coiled or wound around the catheter 15 several times. Then, a thin walled electrode sleeve 22 constructed according to the teachings of the present invention is slid over the tip electrode 13 to a position directly over the coiled conductor end portion 19 as shown in FIGS. 2 and 3.

Once positioned over the coiled conductor end portion 19, as shown in FIG. 3, the electrode sleeve 22 is compressed, such as by swaging or crimping, over the conductor 16 to form a compression contact with the bared conductor end portion 19. The circumference of the sleeve 22 is compressed just far enough to form an isodiametric assembly 10, that is, an assembly 10 where the outer diameters of the catheter 15 and of the sleeve 22 are identical.

The isodiametric configuration of the electrode assembly 12 is best illustrated in FIG. 4 where it will be seen that the sleeve 22 is compressed just far enough so that its outer diameter is the same as the outer diameter of the flexible catheter 15 immediately adjacent the sleeve 22 to form a smooth outer surface to the electrode assembly 12.

In practicing the foregoing method of making the pacing lead 11, the compression contact formed between the sleeve 22 and the coiled conductor 16 is simple to make and requires no extraneous material such as solder to complete the connection.

Further, by coiling the wire conductor end portion 19 several times about the catheter 15, a large contact area between the conductor end portion 19 and sleeve 22 is obtained.

According to the teachings of the present invention, the sleeve 22 is made of a rhenium/tungsten alloy. Empirical tests have shown this alloy to possess properties superior to the properties of the materials previously used in the formation of electrode rings or sleeves. In this respect, such tests have shown the following:

| MATERIAL | COST | DUCTILITY | RADIO-OPACITY | STIMU-LATION |
|---|---|---|---|---|
| Rhenium/Tungsten | high | very good | very good | good |
| Tantalum | high | very poor | good | fair |
| Platinum/Iridium | high | fair | good | good |
| 304 Stainless | low | fair | poor | fair |

From the above comparison, it is apparent that one electrode sleeve alloy material, the rhenium/tungsten alloy, provides an electrode assembly 10 having enhanced radio-opacity characteristics and with stimulation and sensing properties similar to and better than those of platinum/iridium alloys previously used.

In one preferred embodiment of the electrode sleeve 22 the percentage (by weight) of rhenium was between 80% and 99%. The tip electrode 13 also can be made of the rhenium/tungsten alloy.

From the foregoing description, it will be apparent that the method for forming a pacing lead 11 and the specific electrode sleeve 22 thereof constructed according to the teachings of the present invention have a number of advantages some of which have been described above and others of which are inherent in the invention. Also, modifications can be made to the method and lead of the present invention without departing from the teachings of the present invention. Accordingly, the scope of the invention is only to be limited as necessitated by the accompanying claims.

I claim:

1. A pacing/sensing lead comprising a catheter; first and second conductors in said catheter; a tip electrode fixed to the distal end of said catheter and in electrical contct with a distal end of said first conductor within said catheter; said catheter having an opening in the wall thereof; a bared end portion of said second conductor extending through said opening, out of said catheter, and around said catheter; a thin walled electrode sleeve made of rhenium/tungsten alloy positioned about and in direct electrical contact with said bared end portion of said second conductor and compressed about said conductor end portion and said catheter to an extent where the outer diameter of said sleeve is substantially the same as the outer diameter of said catheter, said alloy having as its major component at least 80% rhenium by weight.

2. The lead of claim 1 wherein said bared end portion of said second conductor is coiled several times around said catheter to provide a large contact area between said second conductor end portion and said sleeve.

3. The lead of claim 1 wherein said tip electrode is also made of the rhenium/tungsten alloy.

4. The lead of claim 1 wherein the percentage by weight of rhenium in said alloy is no less than 80% and no greater than 99.9%.

5. The lead of claim 1 wherein said sleeve is compressed about and into direct electrical contact with said second conductor bared end portion by swaging.

6. The lead of claim 1 wherein said sleeve is compressed about and into direct electrical contact with said second conductor bared end portion by crimping.

7. A method of making a pacing/sensing lead comprising the steps of: fixing a tip electrode onto the distal end of a flexible catheter; connecting a distal end of a first wire conductor fed through the flexible catheter to said tip electrode; feeding a second wire conductor part way into the flexible catheter and through an opening in the wall of said catheter; baring the distal end of said second wire conductor; coiling the bared end of said second wire conductor about the catheter; positioning an electrode sleeve made of a rhenium/tungsten alloy over the coiled bared wire conductor end portion such that the outer diameter of said sleeve is substantially the same as the outer diameter of said catheter, said alloy having as its major component at least 80% rhenium by weight.

8. The method of claim 7 including the step of forming said tip electrode from the same rhenium/tungsten alloy from which said sleeve is made.

9. The method of claim 7 wherein said alloy is formed to have a percentage of rhenium by weight no less than 80% and no greater than 99.9%.

10. The method of claim 7 including the step of swaging said sleeve around said second conductor bared end portion and catheter.

11. The method of claim 7 including the step of crimping said sleeve around said second conductor bared end portion and catheter.

12. In a pacing/sensing lead distal electrode assembly comprising at least one sleeve electrode, the improvement residing in said sleeve electrode being made of a rhenium/tungsten alloy having as its major component at least 80% by weight rhenium.

13. The sleeve electrode of claim 12 wherein the percentage of rhenium by weight in said allow is no less than 80% and no more than 99.9%.

* * * * *